US006833506B2

United States Patent
Wechsler

(10) Patent No.: US 6,833,506 B2
(45) Date of Patent: Dec. 21, 2004

(54) TRANSMISSION CABLE FOR MEDICAL SIGNAL VALUES

(75) Inventor: Peter Wechsler, Heideck (DE)

(73) Assignee: Leoni Kabel GmbH & Co KG, Nürnberg (DE)

(*) Notice: Subject to any disclaimer, the term of this patent is extended or adjusted under 35 U.S.C. 154(b) by 0 days.

(21) Appl. No.: 10/293,411

(22) Filed: Nov. 13, 2002

(65) Prior Publication Data

US 2003/0056971 A1 Mar. 27, 2003

Related U.S. Application Data

(63) Continuation-in-part of application No. PCT/EP02/02773, filed on Mar. 13, 2002.

(51) Int. Cl.[7] .............................................. H01B 17/00
(52) U.S. Cl. ................... 174/113 R; 174/47; 174/113 C
(58) Field of Search ............................. 174/113 R, 47, 174/113 C

(56) References Cited

U.S. PATENT DOCUMENTS

| 5,491,299 A | * | 2/1996 | Naylor et al. ................. 174/36 |
| 6,171,255 B1 | | 1/2001 | Ise et al. |
| 6,213,995 B1 | * | 4/2001 | Steen et al. ................. 604/527 |

FOREIGN PATENT DOCUMENTS

| EP | 0 553 372 A | 8/1993 |
| EP | 0 685 239 A | 12/1995 |

* cited by examiner

Primary Examiner—Dean A. Reichard
Assistant Examiner—Jinhee Lee
(74) Attorney, Agent, or Firm—Henry M. Feiereisen; Ursula B. Day

(57) ABSTRACT

In a transmission cable (1) for medical signal values, several single cables (2,5,6,7) of different cable type are integrated in a common cable sheath (3), wherein each cable type is configured for transmission of a particular medical signal value; the multifunctional transmission cable (1) is thus used in particular for integration of the signal values for temperature and nitrogen content in blood as well as ECG and blood pressure.

11 Claims, 1 Drawing Sheet

TRANSMISSION CABLE FOR MEDICAL SIGNAL VALUES

CROSS-REFERENCES TO RELATED APPLICATIONS

This application is a continuation-in-part of prior filed copending PCT International application no. PCT/EP 02/02773, filed Mar. 13, 2002, which designated the United States and on which priority is claimed under 35 U.S.C. §120, the disclosure of which is hereby incorporated by reference.

This application claims the priority of German Patent Application, Serial No. 101 12 051.6, filed Mar. 14, 2001, pursuant to 35 U.S.C. 119(a)–(d), the disclosure of which is incorporated herein by reference.

BACKGROUND OF THE INVENTION

The present invention relates to a transmission cable for medical signal values, in particular electrocardiogram (ECG) values, temperature values, nitrogen values and blood pressure values.

Different cable types are generally used for transmission of such signal values in the medical field. For example, the transmission of electrocardiogram (ECG) values, temperature values, and nitrogen values involves, in general, the use of electric conductors with a metallic conductor core which is enclosed by a conductor insulation, while flexible waveguides are used for transmission of blood pressure values. The result is an undesired cumbersome cabling, when transmission of signal values for medical purposes is involved.

It would therefore be desirable and advantageous to provide an improved transmission cable which obviates prior art shortcomings and which is simple in construction and simplifies a cabling for transmission of medical signal values as far as possible

SUMMARY OF THE INVENTION

According to one aspect of the present invention, several cables of different cable type are surrounded by a common cable sheath and integrated therein in such a way that a single, practicality multifunctional transmission cable is made available for medical signal values, whereby each cable type is configured for transmission of particular medical signal values. The configuration of the transmission cable is hereby suitably symmetrical, wherein the single cables are distributed in an annular space formed about the circumference of a central, special single cable.

Suitably, several single cables are provided per cable type for transmission of the respective particular medical signal value within the transmission cable. For example, transmission of temperature values may involve the use of two or three single cables of same cable type. Likewise, transmission of electrocardiogram values may involve the use of two or also more, e.g., six single cables of same type. Transmission of values commensurate with the nitrogen content in blood may be implemented with two to five single cables. Hereby, the transmission of these signal values may be implemented again by providing different cable types, especially in addition as an alternative, of single cables composed of symmetrical or coaxial cables twisted together.

Transmission of blood pressure values, i.e. of signal values resulting from blood pressure measurements, is implemented by using a flexible tube, designated hereinafter as waveguide and arranged advantageously in central disposition within the transmission cable. Spaced about its outer circumference are then the remaining single cables. Hereby, these remaining single cables are suitably positioned in an annular space between the tube and the outer sheath or cable sheath of the transmission cable, which sheath is common to all single cables.

Depending on the number of single cables surrounding the tube, gaps or intermediate spaces in the annular space can be eliminated by providing a respective number of filler elements, so that the annular space is completely filled. This, in turn, leads to a spatially homogeneous and thus to a particularly advantageous symmetrical configuration of the transmission cable. Hereby, the single cables arranged in the annular space as well as the filler elements have each at least approximately the same outer diameter in order to attain a substantially symmetrical and stable overall configuration as well as a uniform outer contour of the transmission cable. A bandage, made e.g. of nonwoven material, may be provided between the annular space and the tube for increasing the tensile strength of the transmission cable.

The present invention resolves prior art problems by providing a single multifunctional transmission cable or multifunctional cable for medical purposes, which integrates several single cables of different cable type for transmission of particular medical signal values in a common cable sheath, and which unites especially the functional values ECG, temperature, nitrogen content in blood, and blood pressure measurement, are united. Since at least these medical signal values can be transmitted with this single multifunctional cable, the cabling complexity is practically minimized.

BRIEF DESCRIPTION OF THE DRAWING

Other features and advantages of the present invention will be more readily apparent upon reading the following description of a currently preferred exemplified embodiment of the invention with reference to the accompanying drawing, in which the sole

DETAILED DESCRIPTION OF PREFERRED EMBODIMENTS

Figure 1:
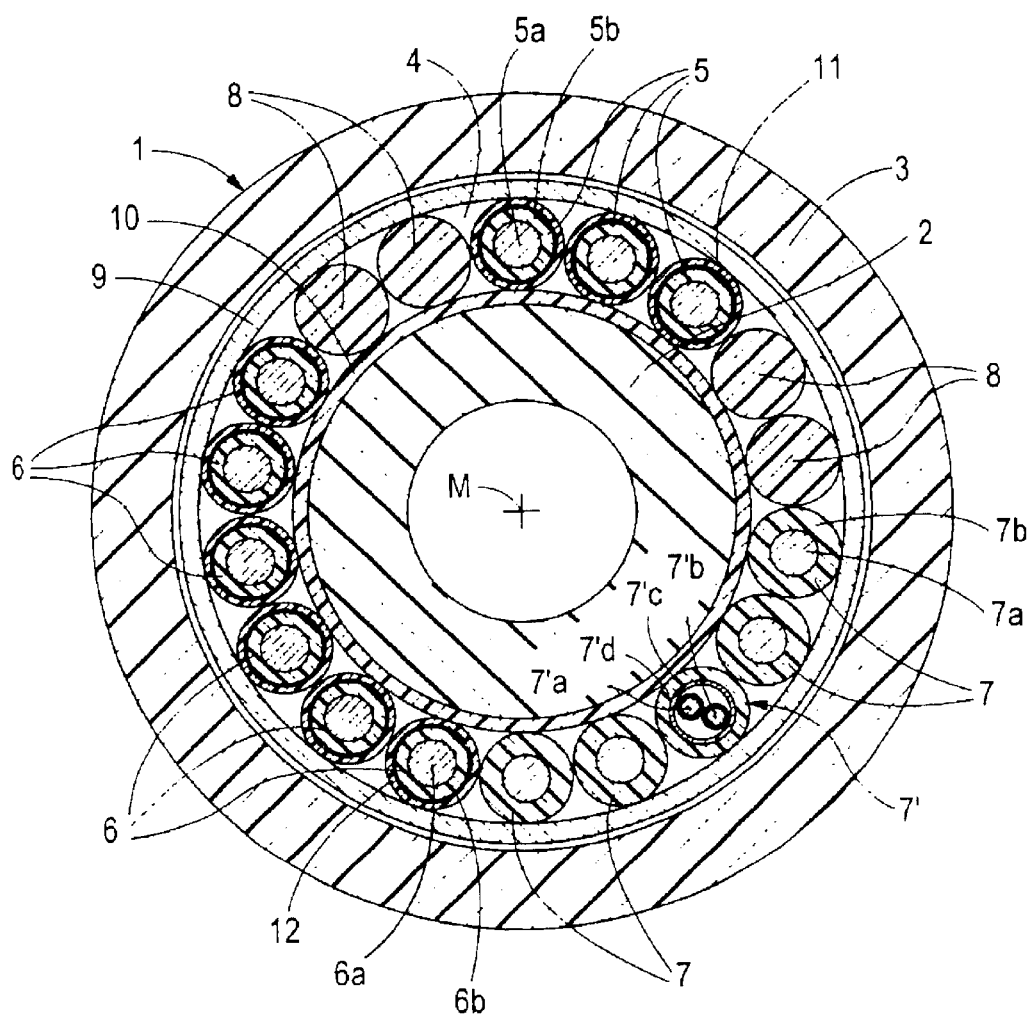
FIG. 1 shows a cross-sectional view of a transmission cable according to the invention for medical purposes with a number of single cables of different cable type. The depicted embodiment is to be understood as illustrative of the invention and not as limiting in any way

Turning now to FIG. 1, there is shown a cross-sectional view of a transmission cable according to the invention, generally designated by reference numeral 1 and designated hereinafter as multifunctional cable, for transmission of different medical signal values. The transmission cable 1 includes a waveguide or tube 2, which is disposed in coaxial surrounding relationship to the cable or center longitudinal axis M and thus centrally arranged. An annular space 4 is defined between the tube 2, as particular single cable for transmission of blood pressure values, and a cable sheath or cable outer sheath 3, for accommodating a plurality of single cables 5, 6, 7, 7' of different cable type. The cable sheath 3 is made, advantageously, of a thermoplastic material, e.g. on the basis of urethane.

A first number of single cables 5, in the exemplified embodiment three single cables 5, for transmission of temperature values are arranged in the annular space 4. A further number of single cables 6, in the exemplified embodiment six single cables 6, are provided for transmission of electrocardiogram or ECG values. Further single cables 7, 7' are provided for transmission of signal values commensurate with the nitrogen content in blood.

In dependence on the number of single cables 5, 6, 7, 7' of different cable type, there are provided in the annular space 4 a number of filler elements 8, in the exemplified embodiment four filler elements 8, for filling the annular space 4. A screen 9 is provided between the annular space 4 and the cable sheath 3 for shielding the annular space and thus the single cables 4 to 7 and 7' against the cable sheath 3 and therefore against the surroundings. The screen 9 may suitably be made as wire mesh in the form of interconnected single wires or as metal foil. A bandage 10, preferably in the form of a nonwoven material, is provided between the annular space 4 and the waveguide 2.

The outer diameter of the single cables 5, 6, 7 as well as of the filler elements 8 are suited to one another so that the width of the annular space 4 is at least substantially equal over the entire circumference of the tube 2. As a consequence, a transmission or multifunctional cable 1 is realized which is symmetrical about the center axis M. Hereby, in particular the single cables 5 and 6 are sheathed by a respective outer sheath 11 and 12, respectively, in order to ensure an outer diameter which corresponds to the single cables 7 and the filler elements 8.

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed as new and desired to be protected by Letters Patent is set forth in the appended claims and their equivalents:

1. A transmission cable for medical signal values, comprising a plurality of single cables of different cable type integrated in a common cable sheath, each said cable type is configured for transmission of a particular medical signal value with one of the single cables configured as a flexible waveguide for transmission of blood pressure values, and wherein a first set of the single cables is provided for collecting values for the nitrogen content in blood, a second set of the single cables for temperature values, and a third set of the single cables for electrocardiogram values, and wherein the waveguide is configured as a single cable of hollow tube-shaped configuration in coaxial disposition around a central axis of the cable sheath and surrounded by an outer circumference, which forms an annular space between the waveguide and the cable sheath for accommodating, all remaining single cables arranged in the annular space, and wherein the annular space is provided with shielding relative to the cable sheath.

2. Transmission cable according to claim 1, wherein a screen is provided between the annular space and the cable sheath.

3. Transmission cable according to claim 1, wherein a bandage is provided between the annular space and the tube.

4. Transmission cable according to claim 1, wherein a number of filler elements are arranged in the annular space.

5. Transmission cable according to claim 1, wherein a thermoplastic material is used as insulating material for the cable sheath.

6. A multifunctional signal transmission cable assembly, comprising:

a cable sheath; and a cable arrangement received within the cable sheath configured for transmission of different medical signal values, wherein the cable arrangement includes a first cable for transmission of a signal commensurate with a blood pressure measurement, a plurality of second cables for transmission of a signal commensurate with a measurement of a nitrogen content in blood, a plurality of third cables for transmission of a signal commensurate with a measurement of temperature values, and plurality of fourth cables for transmission of a signal commensurate with electrocardiogram values, wherein the first cable is a waveguide configured as a single cable in the form of a flexible hollow tube having an outer circumference and arranged in a central disposition within the cable sheath at a distance to the cable sheath to thereby define an annular space between the outer circumference and the cable sheath, said second, third and fourth plurality of cables placed about the circumference of the waveguide in the annular space between the wave guide and the cable sheath.

7. The cable assembly of claim 6, further comprising a screen disposed between the annular space and the cable sheath.

8. The cable assembly of claim 6, further comprising a bandage disposed between the annular space and the first cable.

9. The cable assembly of claim 6, further comprising at least one filler element for use in the presence of a vacant space between neighboring cables in the annular space for filling said vacant space.

10. The cable assembly of claim 9, wherein the plurality of second, third and fourth cables of the cable arrangement, each have a substantially same outer diameter, said filler arrangement including a filler having an outer diameter substantially corresponding to the outer diameter of each of the cables.

11. The cable assembly of claim 6, wherein the cable sheath is made of thermoplastic material.

* * * * *